US006174726B1

(12) United States Patent
Staege et al.

(10) Patent No.: US 6,174,726 B1
(45) **Date of Patent: *Jan. 16, 2001**

(54) METHOD FOR THE IMMORTALIZATION OF CELLS USING CONDITIONALLY TRANSFORMED HELPER CELLS

(75) Inventors: Martin Staege; Georg Bornkamm; Bettina Kempkes, all of Munich (DE)

(73) Assignee: GSF-Forschungszentrum fuer Umwelt und Gesundheit GmbH, Oberschleissheim (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/283,925

(22) Filed: Apr. 1, 1999

(30) Foreign Application Priority Data

Apr. 9, 1998 (DE) ........................................ 198 16 116

(51) Int. Cl.[7] ........................... C12N 15/00; C12N 5/10; C12N 5/12; C12N 5/22; C12N 5/24

(52) U.S. Cl. ......................... 435/449; 435/325; 435/344; 435/346; 435/366; 435/372; 435/372.2; 435/377; 435/451; 435/455; 435/456

(58) Field of Search .................................. 435/325, 344, 435/346, 366, 372, 372.2, 375, 377, 455, 456, 467, 449, 451

(56) References Cited

U.S. PATENT DOCUMENTS 5,629,159 * 5/1997 Anderson ................................ 435/6

FOREIGN PATENT DOCUMENTS 195 41 844 C1 7/1997 (DE) .
196 26 830 A1 1/1998 (DE) .
196 35 568 C1 3/1998 (DE) .

* cited by examiner

*Primary Examiner*—Robert A. Schwartzman
(74) *Attorney, Agent, or Firm*—Townsend and Townsed and Crew LLP

(57) ABSTRACT

The invention is directed to a method for the preparation of a conditionally immortalized immortalization-helper cell (fuseme), the fusemes generated by said method, hybridoma cells prepared using said fusemes as well as a method for immortalization of mammalian cells using said fuseme cells. Further, the invention relates to the generation of T cells directed agaist tumor cells using a fuseme cell.

36 Claims, 3 Drawing Sheets

File: Data.003

| Quad | % Gated |
|---|---|
| UL | 98.74 |
| UR | 1.26 |
| LL | 0.00 |
| LR | 0.00 |

File: Data.004

| Quad | % Gated |
|---|---|
| UL | 78.86 |
| UR | 21.14 |
| LL | 0.00 |
| LR | 0.00 |

File: Data.004

| Quad | % Gated |
|---|---|
| UL | 86.00 |
| UR | 8.66 |
| LL | 2.94 |
| LR | 2.40 |

File: Data.004

| Region | % Gated |
|---|---|
| R1 | 27.54 |
| R2 | 100.00 |
| R3 | 0.00 |
| R4 | 89.01 |

File: Data.004

| Region | % Gated |
|---|---|
| R1 | 83.10 |
| R2 | 0.00 |
| R3 | 100.00 |
| R4 | 7.25 |

File: Data.004

| Quad | % Gated |
|---|---|
| UL | 5.76 |
| UR | 5.18 |
| LL | 1.34 |
| LR | 87.72 |

METHOD FOR THE IMMORTALIZATION OF CELLS USING CONDITIONALLY TRANSFORMED HELPER CELLS

PATENT SPECIFICATION

The invention relates to a method for the preparation of a conditionally immortalized helper cell (fuseme), the hybridoma cells prepared using said fusemes as well as a method for immortalization of mammalian cells using the fuseme cells. Furthermore, the invention relates to the generation of T cells directed against tumor cells using a fuseme cell.

BACKGROUND OF THE INVENTION

Many medical or biological problems involve the requirement or desire to generate a great number of cells in vitro out of a starting material of few cells in order to conduct scientific experiments or to work with these cells in the context of a therapeutical intervention. The expansion of cells frequently imposes a problem since cells generally have a limited growth capacity. For example, this is also true for many tumor cells which often show a growth disadvantage in vitro as compared to normal cells making an expansion of these cells difficult [Lange (1998), Visonneau et al. (1995)]. One possibility to expand cells in vitro is to stimulate the cells with appropriate stimuli (cytokines, suitable feeder cells, stimulation of appropriate receptors on the cell surface, etc.) to enable the growth or the survival, respectively, of said cells. However, also in this case it is generally impossible to expand the cells to any number, and the cells will cease to grow after some time. Moreover, the stimulation conditions for many cell types are unknown to date so that this method may not be universally employed. Although the "culture" of different tumor cells in living immunodeficient experimental animals may be performed for a prolonged time [Visonneau et al. (1995)], this method is elaborate and, moreover, must be rejected principally for ethical reasons.

An elegant way to overcome this problem is genetical immortalization of the desired cells [Hubbard & Ozer (1995), MacDonald (1994)]. Indeed, some tumor cell lines have the capability of dividing practically indefinitely also in vitro, i.e. are immortalized. Previously, this led to the development of the technique of cell fusion between the tumor cells and the cells for which immortalization was desired resulting in the pioneering development of monoclonal antibodies [Köhler & Milstein (1975), Peters et al. (1988)). However, particularly for the immortalization of human cells no optimal fusion partners are available to date [Gordon (1989)]. For this reason, the method of fusing human cells with suitable cells of rodents is frequently used but the resulting hetero-species hybridomas have the unfavorable property of being cytogenetically unstable and to lose individual chromosomes (often the important ones and in the case of human/rodent hybridomas preferably the human ones) by time.

A group of promising human fusion partners is represented by Epstein-Barr virus (EBV) transformed lymphoblastoid cell lines (LCLs). In particular, these cells may be easily established [Walls and Crawford (1987)]. However, for many applications these cells have undesirable properties. Thus, the expression of some viral proteins results in an inhibition of the synthesis of immunoglobulins, a property which e.g. hinders the generation of human monoclonal antibodies. Besides, the antigens expressed by EBV in LCLs induce a strong immune response which may exceed all other immune responses. This is disadvantageous if it is desired to perform a fusion between a LCL and a tumor cell to employ the hybridoma afterwards in the stimulation of an immune reaction against antigens. However, another property of these cells has proven to be particularly favorable in the induction of an immune reaction. Regarding their immunostimulatory capabilities LCLs belong to the most potent cells available. Therefore, it may be expected that hybridomas of a tumor cell and a LCL also have all co-stimulatory molecules in addition to the tumor-specific antigens to efficiently induce an immune response.

It is an object of the present invention to provide a method enabling the preparation of cells which may be used in transferring the information for immortalization to another cell.

SUMMARY OF THE INVENTION

According to the invention, this object has been solved by the method characterized in more detail in claim 1 which serves to provide conditionally immortalized cells, in following referred to a "fuseme". This cell may be regarded as a helper cell since it "helps" to immortalize another cell. The method of preparation of a conditionally immortalized immortalization-helper cell consists of at least the following steps:

(a) Introducing immortalizing genes into mammalian cells in a way that at least the expression and/or function of at least one of said genes may be controlled in order to obtain conditionally immortalized mammalian cells;

(b) introducing a least two selectable markers for positive and negative selection to enable the selection between fuseme cells, the cells to be immortalized using the fuseme cells and the cells immortalized by the fuseme cells;

(c) selecting for such cells (fusemes) carrying the selectable marker introduced in step (b) and being conditionally immortalized.

As the mammalian cells there may be employed any cell capable of being immortalized. Preferably, those cells are human cells or rodent cells. Examples for such cells are lymphocyte cells or fibroblast cells. As the lymphocyte cells for example B cells or T cells may be conditionally immortalized.

Conditional immortalization of mammalian cells is known per se [Kempkes et al. (1995), Wyllie et al. (1993)]. For this purpose, the genes necessary for the immortalization of a cell must be introduced into a mammalian cell. Introduction of the genes may be performed e.g. by infection with a virus containing the genes or by transfection of the DNA.

Genes capable of immortalizing cells are known per se. These include for example the immortalizing genes of EBV, adenoviruses, HTLV-1 or oncogenes. These genes may be introduced into the mammalian cells to be conditionally immortalized by means of vectors which vectors include viruses, plasmids, cosmids etc. according to the invention. The genes responsible for immortalization are in each case engineered to enable a conditional expression or regulation of the function of the immortalizing genes. For example, these genes may be deleted from a viral genome on which they are naturally present, for example from EBV, the information required for immortalization is introduced to a plasmid and the expression of the immortalizing genes on the plasmid or the function of these genes may be conditionally regulated using suitable methods which are presented by way of example in this application. Examples for vectors for introduction of the immortalizing genes are EBV, adenoviruses, retroviruses, foamy viruses, pox viruses or SV40 as well as vectors derived from said viruses. An example for a vector derived from EBV are mini-EBV vectors. An example for a pox virus is the vaccinia virus.

The immortalizing genes of the aforementioned viruses or the oncogenes enabling an immortalization, respectively, are examples for oncogenes known per se useful in the immortalization of mammalian cells which are c-myc, c-abl, c-ras, and combinations of these oncogenes; immortalizing genes of EBV are for example EBNA2 and LMP1.

The method according to the present invention provides a fuseme cell at least characterized by the following properties:

(a) mammalian cell which is conditionally immortalized;

(b) having at least two selectable markers for positive and negative selection enabling the selection between fuseme cells, cells to be immortalized and immortalized cells.

The fuseme cell described above can be used for preparing monoclonal antibodies producing cell line and for preparing a T/B hybridoma cell line.

The fuseme cells obtained by the invention described above are employed as helper cells to immortalize mammalian cells. For this purpose, a fuseme cell and a mammalian cell to be immortalized using the fuseme cell are contacted so that the feature of immortalization is transferred from the fuseme cells to the cells to be immortalized by means of the fuseme cells. Afterwards, selection for those cells is performed which carry the feature of immortalization. This may be effected for example by coupling the immortalization feature with a selectable marker for which the selection is carried out.

In another embodiment the fuseme cells have been immortalized and are fused with the cell to be immortalized resulting in an already immortalized hybrid cell. Moreover a selection for growing cells may be carried out since only immortalized cells are capable of indefinite growth.

As the mammalian cell to be immortalized any mammalian cell capable of immortalization may be employed. Examples for these cells are lymphocyte cells or fibroblast cells. Examples for lymphocyte cells are B cells and T cells. As the cell to be immortalized, also a tumor cell may be used. An example for a tumor cell is a leukemic cell. Mostly, tumor cells are not capable of indefinite growth in vitro. This may be generally due to insufficient culture conditions. Thus, for example in the case of malignant melanoma, a tumor regarded as well cultivatable, the establishment of a cell line from the tumor is successful in only about 25% of the cases.

Two different methods for the transfer of the immortalization feature from the fuseme cells to the cells to be immortalized are described in more detail below. In the first method viral particles are released from the fuseme cell containing the genes necessary for immortalization of a cell. The viral particles will infect the cells to be immortalized if fuseme cells and the cells to be immortalized are co-cultured and will transfer the immortalizing genes by infection. In the second method the fuseme cells are fused with the cells to be immortalized to create hybridomas carrying both the properties of the fuseme cell and the cell to be immortalized.

In another embodiment of the present invention the hybridoma cells are obtained by fusion of a B cell which has been conditionally immortalized by EBV with a leukemic cell. Such hybridoma cells may be employed in the establishment of T cells able to recognize unfused leukemic cells. The method for the preparation of T cells directed against tumor cells, preferably leukemic cells, may be outlined as follows:

(a) Providing a fuseme cell and a tumor cell to be immortalized by means of the fuseme cell;

(b) transferring the feature of immortalization from fuseme cells to the tumor cells to be immortalized by means of the fuseme cells;

(c) selecting for immortalized tumor cells;

(d) recovering the immortalized tumor cells, abolishing the conditional immortalization and co-culturing with peripheral mononucleated cells containing T cells of the patient from whom the tumor cell has been obtained or of a healthy donor;

(e) selecting for T cells capable of recognizing the tumor cells employed in step (a).

Hence, it is evident that the T-cells selected in step (e) are capable of recognizing the tumor cells employed in step (a) selectively. Selectively means that said T-cells are capable of recognizing the tumor cells in step (a) but not fuseme cells employed in step (b) and particularly not only the immortalized tumor cells employed in step (d). When using the T-cells obtained in step (e) in therapeutic methods, it may be generally desirable that the T-cells are capable of recognizing only said tumor cells and generally not all cells of the patient. Therefore, graft versus host reactions on a level threatening the life of said patients are avoided. In a further embodiment of the invention hybridomas may be generated by fusing the fuseme cells and the lymphocyte cells which for example produce an antibody or a T cell receptor having the desired specificity. Such a method may for example be performed as follows:

(a) Providing a fuseme cell and a lymphocyte cell;

(b) fusing the fuseme cell with the lymphocyte cell;

(c) selecting for conditionally immortalized hybridoma cells and optionally cloning individual hybridoma cells;

(d) expanding the hybridoma cells; and (e) abolishing the conditional immortalization.

In the following, the present invention will be described in more detail with respect to Examples and Figures. The Examples are embodiments of the invention, however, the invention is not limited to these specific Examples. Within the purview of the original disclosure and the claims, these Examples may be modified.

DESCRIPTION OF THE PREFERRED EMBODIMENTS

Figure 1:
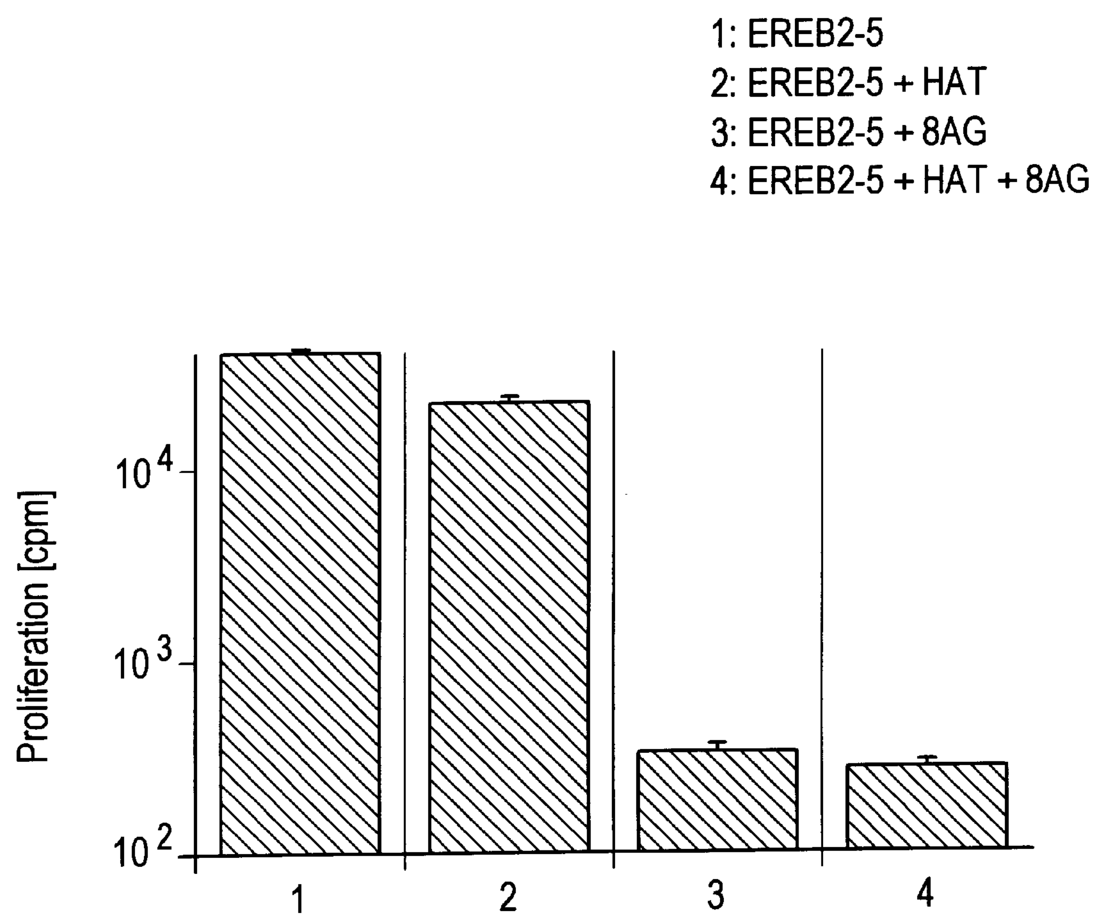
FIG. 1: Effect of HAT and 8AG on EREB2-5 cells.

The method described below is an elegant way to solve the problems known from the prior art. In the following, the invention will be outlined using the development of a prototype of an universally useful helper cell for immortalization of human cells (this cell type is called a fuseme by us since the fusion of these cells with appropriate cells to be immortalized is directed to a preferred embodiment of the present invention). Furthermore, it is possible to culture these cells together with the cells to be immortalized and by this co-culture to effect the transfer of immortalization to the latter cells. Important features of the fusemes are on the one hand conditionality of the immortalization and on the other hand the introduction of two selectable markers into the cells to be conditionally immortalized. One of these markers is suitable to enable the growth of the fusemes and the fusion products of the fuseme and the cell to be immortalized in a medium which otherwise has a toxic effect on cells. With the second selectable marker it is possible to kill unfused fusemes. By both of the selectable markers it is possible to separate fused and unfused cells quickly and efficiently. On the other hand, the conditionality of immortalization makes it possible to use the fused cells after the immortalization function has been switched off independently of the properties of the cells associated with immortalization for experimental and therapeutical uses.

For the first selectable marker, a number of antibiotic resistances are available, e.g. geneticin or hygromycin resistance. For the second marker which makes it possible to kill unfused fusemes particularly the sensitivity of the cells for addition of hypoxanthine, aminopterine, and thymidine (HAT) to the culture medium may be used.

For the introduction of the respective selectable markers into the fusemes several methods are available. Introduction in the context of this application is not only meant to include the introduction of the respective gene into the cells using genetic engineering but also the utilization of naturally occurring mutations mediating resistance or sensitivity, respectively, against an active agent. Thus, cells may be cultured in the presence of 8-azaguanine or bromodeoxyuridine and in this manner cells may be selected which due to spontaneous mutations have a defect in a certain metabolic pathway leading to the synthesis of DNA components. Afterwards, cells treated in this way are unable to grow in a medium also blocking an alternative way for the synthesis of DNA components. However, normal cells are still capable of growing after this pathway has been blocked and will transfer this property also to the fusion products of these cells and the fusemes. Similar methods are also available for the introduction of a specific resistance, for example against ouabain.

In addition, also several ways for conditional immortalization are available. Besides viruses, e.g. EBV, also oncogenes or combinations of several oncogenes, respectively, may be used in immortalization [MacDonald (1994)]. If the expression of said oncogene is rendered controllable as may be easily effected nowadays [e.g. Wyllie al. (1993)] also this method will result in conditionally immortalized fusemes.

Fields of use for the fusemes are abundant. As already mentioned, the use of these cells leads to the production of human monoclonal antibodies which are desirable for numerous fields and in particular in the clinical field. A particularly promising field of use is in the stimulation of immune responses in vitro and in vivo against cells which themselves have only poor immunostimulatory properties. In this respect cancer therapy is our primary concern.

Numerous tumor cells escape the immunological defense because they do not express co-stimulatory signals necessary for an efficient T cell stimulation. On the contrary, the existence of tumor-specific antigens against a number of tumors has been detected, and an important concern in immune therapy in the case of cancer is primarily to achieve an increase in the immunogenicity of the tumor cells or the tumor antigens, respectively. Although numerous tumor antigens have already been cloned, this is not true for a number of tumor types, and it is impossible to predict if a particular tumor of a certain patient will in each case express the respective antigen. For these reasons, it is difficult to carry out a specific therapy in the individual case.

It is the solution of this problem which is the most important advantage of the fuseme technology. By the fusion and immortalization of the tumor cell, properties of the fuseme cell are also transferred to the hybridoma cell. Thus, if LCLs which have been conditionally transformed with EBV are employed as the fuseme in this way also co-stimulatory signals definitely present on the LCL are transferred to the hybridoma. On the other hand, the tumor antigens are transferred from the tumor cell to the hybridoma. Therefore, it is not necessary to know which tumor antigen is expressed in the tumor cell at all. Since the hybridoma cell has been conditionally immortalized, immortalization-specific antigens may be switched off and thereby the immune response may be focussed on the actual tumor antigens. In addition, also the specificities of the established T cells may be determined afterwards, and in this manner further tumor antigens may be determined.

Method

1.) Establishment of a conditionally immortalized universal immortalization helper cell (fuseme)

Suitable cells e.g. human lymphocyte cells, human B cells or T cells are conditionally immortalized by means of an appropriate method. For this purpose e.g. in the case of B cells, an EBV such as the EBV strain P3HR1 carrying a deletion in the EBNA2 gene required for immortalization may be employed. Thus, this viral strain has lost its B cell transforming properties. However, the defect may be complemented if the missing EBNA2 is introduced into the same cell on another plasmid. B cells containing the P3HR1 virus and in addition a functional EBNA2 on an appropriate expression vector start to proliferate indefinitely. If a fusion protein of EBNA2 and the hormone binding domain of the estrogen receptor is used instead of wild type EBNA2 conditionally immortalized cells will be conveniently obtained [Kempkes et al. (1995)]. These cells are only capable of growth in the culture medium in the presence of estrogen and cease to grow after estrogen depletion. It is also possible to place a resistance gene for a suitable active agent e.g. geneticin on another or the same plasmid enabling the expression of the ER/EBNA2 fusion protein. Thereby, the conditionally immortalized cells will be at the same time provided with a positive selectable marker for later selection of the hybridomas.

By culturing the thus established conditionally immortalized cells in the presence of 8-azaguanine or bromodeoxyuridine cells will be selected which are resistant against said active agent. These cells will simultaneously become sensitive for a mixture of hypoxanthine, aminopterine and thymidine (HAT). Thereby the cells are provided with a second selectable marker, in this case for negative selection. The product represents the desired fuseme.

2.) Immortalization transfer to the cells to be immortalized and selection of immortalized cells a) Transfer by cell fusion In this method the immortalization of the desired cell is performed by fusion with the fuseme. This fusion may be for example induced by polyethylene glycol. Since the fuseme is resistant against e.g. geneticin and 8-azaguanine the resulting hybridomas may be rapidly selected out of unfused fusemes and unfused other cells by cultivation in HAT and geneticin.

b) Transfer by co-cultivation

If the cell to be immortalized and the fuseme are of the same primary cell type (such as both are derived from B cells) and immortalization of the fuseme was performed using transforming viruses which may be released from the fuseme in the form of infectious particles, immortalization transfer is possible by co-cultivation of the fuseme with the cell to be immortalized. Since the fuseme is resistant against 8-azaguanine the resulting immortalized cells may be separated from residual helper cells by cultivation in the presence of HAT. If the problem arises that other undesired cells (in the case of immortalization of cells obtained from blood these may be for example contaminating T cells or endogenous EBV-transformed cells) adversely affect the growth of the cells, the cells may be effectively prevented from growing by means of the second, positive selectable marker, i.e. for example geneticin.

Because the fusemes have been provided with a negative selectable maker (e.g. HAT sensitivity) it is possible, if desired, to effect immortalization of a target cell in a two-step process. However, a prerequisite for this method is that the conditional immortalization of the fuseme has been performed using a suitable vector which may be released from the fuseme and is capable of re-immortalizing a new cell in a conditional manner. Required for this method is merely a prototype of a fuseme the establishment of which by us is described in the following.

Establishment of a Prototype Fuseme

The establishment of a fuseme is described which has been generated according to the invention and which at the moment is the first and only cell line of this type. This fuseme has been called ZAGREB. To establish the ZAGREB fuseme line an already described cell line (EREB2-5) [Kempkes et al. (1995)] served as the starting material. These cells were generated by simultaneous infection of cells from umbilical cord blood with the P3HR1 EBV virus and an expression plasmid enabling the expression of an ER/EBNA2 fusion protein. These cells will only grow in the presence of estrogen in the culture medium. After estrogen depletion many EBV antigens will no longer be expressed and the expression of endogenous immunoglobulin is markedly increased. Thereby, this cell provides several positive features because of which it appeared useful for the subsequent establishment of a fuseme. Since these cells are also resistant against geneticin the introduction of a positive selectable marker into the cells became obsolete.

For this purpose, the cells ($4\times10^7$ in 40 ml RPMI1640+ 10% FCS+Pen/Strep, 50 U ($\mu$g)/ml+amphotericin B 750 ng/ml) were grown in the presence of estrogen (1 $\mu$M) and 8-azaguanine (8AG, $6.6\times10^{-3}$ M). Under these conditions, most of the cells died within the first 4 weeks. At this point the surviving cells were sedimented by centrifugation (1000 rpm, 10 min) and resuspended in 20 ml of fresh medium with the same additions. Because of the medium change and the fresh estrogen the cells started to proliferate strongly. According to our surprising observations it is significantly easier to render conditionally immortalized LCLs 8AG-resistant than classical LCLs.

Figure 2:
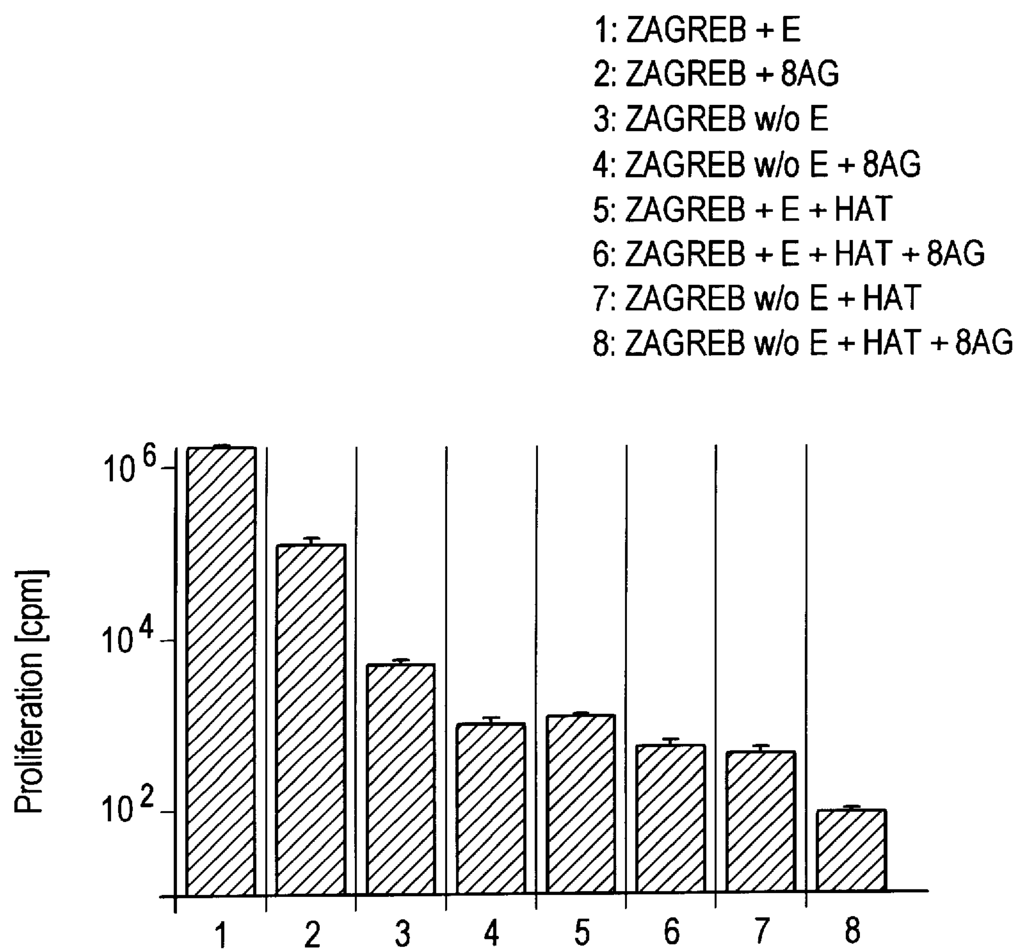
FIG. 2: Effect of estrogen, HAT and 8AG on ZAGREB cells.

The established 8AG-resistant cell line (ZAGREB) was tested for its HAT sensitivity. EREB2-5 cells ($2\times10^4$/well) were cultured in the presence or absence of HAT or 8AG, respectively, for 5 days in microtiter plates, the last 24 h of which were in the presence of $^3$H-thymidine. The incorporation of radioactive thymidine into the DNA was detected by means of liquid scintillation counting. As shown in FIG. 1 the starting cell line EREB2-5 is resistant against HAT and sensitive for 8AG. In contrast, the ZAGREB cells are 8AG-resistant and HAT-sensitive (FIG. 2). For this Figure, ZAGREB cells ($2\times10^4$/well) were cultured in the presence or absence of HAT or 8AG, respectively, for 5 days in microtiter plates, the last 24 h of which were in the presence of $^3$H-thymidine. The incorporation of radioactive thymidine into the DNA was detected by means of liquid scintillation counting. Also shown in FIG. 2 is the maintenance of the conditionality of immortalization. In the absence of estrogen the cells cease to grow. Thus, ZAGREB cells are a prototype of a fuseme.

Fusion of these cells using PEG is possible without any problem. As the fusion partner PBMCs of a healthy donor, a Burkitt's lymphoma cell line as well as a human thymoma have been tested.

Immortalization of cells by co-culturing was tested using both PBMCs of a healthy donor and a human cell line of a chronic lymphathic leukemia.

Figure 3:
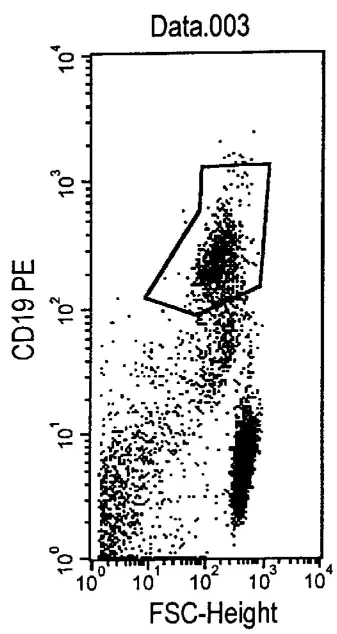
FIG. 3: Hybridoma cells expressing antigens of both fusion partners.
Figure 3:
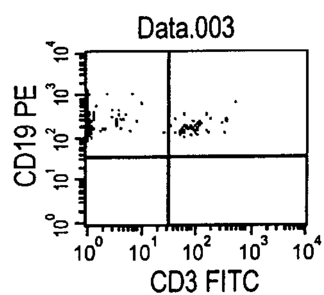
Figure 3:
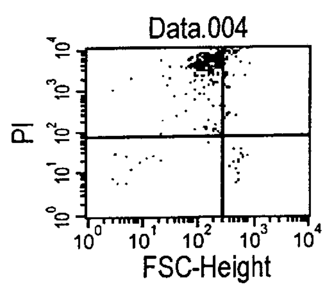
Figure 3:
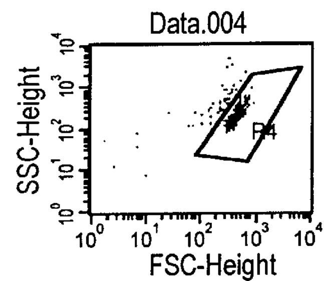
Figure 3:
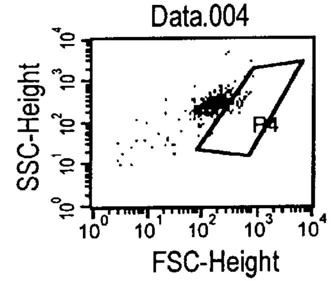
Figure 3:
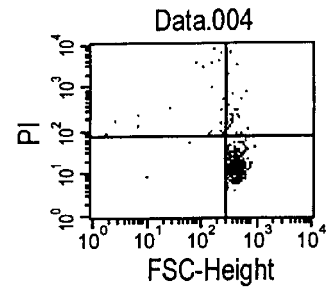

FIG. 3 illustrates the result of a fusion between ZAGREB cells and the human thymoma cell line Jurkat. The abbreviations used in FIG. 3 are as follows:

"QUAD": is short for quadrant (UL=upper left; LR=upper right, etc.;

"% Gated": denotes the percentage of cells localized in one of the respective four quadrants;

"FSC-High": refers to Forward Scattering of the light, a measure for cell size;

"SSC-High": refers to Sideways Scattering of the light, a measure for cell granulation;

"PI": propidium iodide;

"PE": phycoerythrin;

"FITC": fluorescein isothiocyanate

The fusion was performed according to a procedure using ConA-mediated adhesion of the cells to the cell culture dish in order to increase the fusion efficiency (Graessmann et al. (1980)].

Immediately after fusion selection with HAT ($5\times10^{-3}$ M hypoxanthine, $2\times10^{-5}$ M aminopterine, $8\times10^{-4}$ M thymidine) was carried out. After 2 further days the cells were treated with geneticin (250 $\mu$g/ml) to prevent the growth of unfused Jurkat cells. After one week of HAT/geneticin selection, the fused cells were analyzed by FACS. For this purpose, the cells were incubated with medium (DATA 003) or a CD3-specific antibody (DATA 004), washed, and bound antibody was detected by FITC-labeled secondary antibody. Afterwards, the cells were incubated with a CD19-specific PE-labeled antibody and washed. Cells positive for CD19 were electronically gated in (upper left panel) and the percentage of CD19-positive cells which were also CD3-positive was determined. The cells positive for both markers corresponding to fused cells can be clearly seen. It is also clear (lower half of the figure) that the cells positive for both markers exhibit higher Forward Scattering (FSC) of the light as well as lower fluorescence following propidium iodide (PI) staining as compared to only CD19-positive cells. These parameters demonstrate that cells only positive for CD19 enter apoptosis, which was expected in view of HAT selection. As can be clearly seen cells are detectable one week after fusion which are both positive for CD19 (a marker of the ZAGREB cells) and for CD3 (a marker of the Jurkat cells). It is also obvious that compared to the CD19-negative cells the major portion of CD19-positive cells show a markedly lower forward scattering (FSC). This indicates a beginning apoptosis of these cells induced by HAT selection which interpretation has been confirmed by propidium iodide staining [Darzynkiewicz et al. (1995)] which is also shown. Thus, the fuseme is useful for the formation of hybridomas with other cells, in this case a lymphoma. It may be assumed that the hybridoma cells have properties of both fusion partners (see CD19 and CD3). Since CD3 appears associated with the idiotypic (and therefore tumor-specific) T cell receptor on the cellular membrane, this example also shows that hybridomas are able to continue to express a tumor-specific antigen.

This fuseme is suitable as a helper cell to generate other fusemes with the desired properties in order to fuse these with the final target cells. For example, fusemes may be generated of a patient by co-culturing PBMCs of the patient together with ZAGREB cells in a first step. By the addition of HAT to the culture medium the growth of the ZAGREB cells is inhibited. The EBV particles released from the ZAGREB cells are capable of infecting and conditionally transforming B cells of the patient. As soon as growth of the cells is observed any cells may be prevented from growing by addition of geneticin to the culture medium which proliferate without carrying the ER/EBNA2 construct (e.g. alloreactive and EBV-specific T cells or B cells of the patient endogenously infected with EBV) because the geneticin resistance is encoded on this construct. By culturing the cells in 8AG cells will be obtained which behave like ZAGREB cells but carry the genetic markers (e.g. MHC) of the patient. Subsequently, these cells may be fused with tumor cells of the patient and used as vaccines. The only prerequisite for this approach to be successful is that there is enough time for the double immortalization transfer (with an optimal outcome about 8 weeks are required, 4 weeks to establish the fuseme and 4 weeks to render the fuseme HAT-sensitive).

EXAMPLE

Leukemic cells of a patient suffering from acute lymphatic leukemia (ALL) are obtained from peripheral blood. A portion of the cells is stored in liquid nitrogen. A second portion of the cells is fused with a fuseme. As the fuseme in this case are used e.g. ZAGREB cells or other conditionally EBV-immortalized B cells having the properties of the ZAGREB cell line. Immortalization transfer by means of co-culturing is impossible according to our knowledge to date because ALL cells lack an receptor for EBV. Afterwards the desired hybridomas are selected via culture in the presence of HAT and geneticin. In the meantime, the patient has received a bone marrow transplantation (BMT) from an appropriate donor.

Peripheral mononucleated cells (PBMCs) of the BM donor are cultured together with the hybridoma cells following conditional switch-off of immortalization. In this manner the T cells contained in the PBMCs are rendered sensitive both against antigens derived from the fuseme (but not against antigens the expression of which is dependent on immortalization of the fuseme) and against antigens expressed in the leukemic cells. Subsequently, suitable methods ($^{51}$Cr release assay, proliferation assay etc.) are employed to test for the capability of the T cells generated by this procedure to recognize the unfused leukemic cells (which in the meantime were stored in liquid nitrogen). In the positive case the T cells are expanded by repetitive restimulation and tested for their possible graft-versus-host (GvH) activity. In the case of missing GvH activity the generated T cell lines are stored in liquid nitrogen. As soon as the patient shows a recidivation the generated T cells of the BM donor will be adoptively transferred to the patient to induce the healing process. The established fuseme/leukemia hybridoma cell line may used to a) carry out biochemical, cellular biological, moleculargenetic and cytogenetic experimentation, b) to characterize tumor antigens and c) to serve as allogenic vaccine for patients having similar MHC alleles and the same basic disease as the patient.

REFERENCES

Darzynkiewicz, Z., X. Li, J. Gong, S. Hara & F. Traganos, 1995. Analysis of cell death by flow cytometry. In: G. P. Studzinski (ed.), Cell growth and apoptosis (A practical approach). Oxford, IRL Press.

Gordon, J. 1989. Human monoclonal antibodies. In: D. Catty (ed.), Antibodies, vol. 1 (A practical approach). Oxford, IRL Press.

Graessmann, A., H. Wolf & G. W. Bornkamm, 1980. Expression of Epstein-Barr virus genes in different cell types after microinjection of viral DNA. Proc. Natl. Acad. Sci. USA 77:433.

Hubbard, K. & H. L. Ozer, 1995. Senescence and immortalization of human cells. In: G. P. Studzinski (ed.), Cell growth and apoptosis (A practical approach). Oxford, IRL Press.

Kempkes, B., D. Spitkovsky, P. Jansen-Dürr, J. W. Ellwart, E. Kremmer, H.-J. Delecluse, C. Rottenberger, G. W. Bornkamm & W. Hammerschmidt, 1995. B-cell proliferation and induction of early G1-regulating proteins by Epstein-Barr virus mutants conditional for EBNA2. EMBO J. 14:88.

Köhler, G & C. Milstein, 1975. Continuous culture of fused cells secreting antibody of predefined specificity. Nature 256:495.

Lange, B. J., 1989. Growth of human leukaemia cells in vitro. In: R. Baserga (ed.), Cell growth and division (A practical approach). Oxford, IRL Press.

MacDonald, C, 1994. Immortalization of hematopoietic cells. In: Freshney, R. I., I. B. Pragnell & M. G. Freshney (eds.), Culture of hematopoietic cells. New York, Wiley-Liss.

Peters, J. H., H. Baumgarten & M. Schulze, 1988. Monoklonale Antikörper. Berlin, Springer.

Visonneau, S., A. Cesano & D. Santoli, 1995. Growth and activation of human leukaemic cells in vitro and their growth in the SCID mouse model. In: G. P. Studzinski (ed.), Cell growth and apoptosis (A practical approach). Oxford, IRL Press.

Walls, E. V. & D. H. Crawford, 1987. Generation of human B lymphoblastoid cell lines using Epstein-Barr virus. In: G. G. B. Klaus (ed.), Lymphocytes (A practical approach). Oxford, IRL Press.

Wyllie, F. S., J. A. Bond, T. Dawson, D. White, R. Davies & D. Wynford-Thomas, 1993. A phenotypically and karyotypically stable human thyroid endothelial line conditionally immortalized by SV4OT. In: N. Lemoine & A. Epenetos (eds.), Mutant oncogenes. London, Chapman & Hall.

What is claimed is:

1. Method for the preparation of a conditionally immortalized immortalization-helper cell (fuseme) including at least the following steps:

(a) introducing immortalizing genes into mammalian cells in a way that at least the expression and/or function of at least one of said genes may be controlled in order to obtain conditionally immortalized mammalian cells;

(b) introducing at least two selectable markers, one for positive and one for negative selection, into the conditionally immortalized mammalian cells to enable selection among fuseme cells, cells to be immortalized using the fuseme cells and cells immortalized by the fuseme cells;

(c) selecting for such cells (fusemes) carrying the two selectable markers introduced in step (b), the immortalizing gene introduced in step (a), and being conditionally immortalized.

2. Method according to claim 1 wherein as said mammalian cells human cells or rodent cells are used.

3. Method according to claim 1 wherein said immortalizing genes are members selected from the group consisting of genes of Epstein-Barr virus (EBV), genes of adenoviruses, genes of HTLV-1, and oncogenes.

4. Method according to claim 1 wherein vectors of EBV, of adenoviruses, of retroviruses, of foamy viruses, of pox viruses or vectors derived from SV40 are used to introduce said immortalizing genes.

5. Method according to claim 1 wherein said immortalizing genes are members selected from the group consisting of EBNA2 genes, LMP1 genes, and EBNA3a genes.

6. Method according to claim 1 wherein said immortalizing genes may be controlled by hormones or antibiotics.

7. Method according to claim 1 wherein as the selectable marker for positive selection the cells are rendered resistant against an agent and wherein for negative selection the cells are rendered sensitive for an agent.

8. Method according to claim 1 wherein said steps (a) and (b) are carried out simultaneously.

9. Method according to claim 1 wherein the EBNA2 gene of EBV is used as said controllable immortalizing gene, an antibiotic resistance gene is used as said marker for positive selection, a sensitivity for HAT is used as said marker for negative selection, EBV is used for introduction of the immortalizing gene, and a B cell is used as said mammalian cell.

10. Method according to claim 1 wherein the mammalian cells are rendered sensitive for HAT by addition of 8-azaguanine or bromodeoxyuridine.

11. Method according to claim 2 wherein as said mammalian cells lymphocyte cells or fibroblast cells are used.

12. Method according to claim 4 wherein said vectors of EBV are mini-EBV vectors, and/or said vectors of pox viruses are vaccinia viruses.

13. Method according to claim 6 wherein an estrogen or an androgen is used as said hormone.

14. Method according to claim 7 wherein the cells are rendered resistant against an antibiotic and are rendered sensitive for hypoxanthine, aminopterine and thymidine (HAT).

15. Method according to claim 7 wherein the cells are rendered resistant against geneticin, hygromycin or ouabain.

16. Fuseme cell comprising the following features:

(a) a mammalian cell which comprises a controllable immortalizing gene and is conditionally immortalized; and (b) two selectable markers, one for positive and one for negative selection enabling the selection among fuseme cells, cells to be immortalized by means of the fuseme cells, and cell immortalized using the fuseme cells.

17. Method for immortalization of mammalian cells comprising the following steps:

(a) providing fuseme cells and mammalian cells to be immortalized;

(b) providing the mammalian cells to be immortalized with immortalization genes from the fuseme cells; and (c) selecting for mammalian cells so immortalized.

18. Method according to claim 17 wherein a lymphocyte cell or a fibroblast cell is used as said mammalian cell to be immortalized.

19. Method according to claim 17 wherein a tumor cell is used as said mammalian cell to be immortalized.

20. Method according to claim 17 wherein a leukemic cell is used as said mammalian cell to be immortalized.

21. Method according to claim 17 wherein the mammalian cells to be immortalized are provided with immortalizing genes from the fuseme cells by gene transfer.

22. Method according to claim 17 wherein providing the mammalian cells to be immortalized with immortalization genes is accomplished by fusion of said fuseme cells and said mammalian cells to be immortalized.

23. Method according to claim 17 wherein the selection for immortalized cells is accomplished by culturing the cells in a medium neither enabling the growth of said fusemes nor the growth of said cells to be immortalized.

24. Method according to claim 21 wherein the gene transfer is accomplished by transferring viruses released from the fuseme and containing the immortalizing genes and by infection of the mammalian cells to be immortalized by the viruses thus transferred.

25. Method according to claim 22 wherein the cell fusion is induced by polyethylene glycol, electrofusion or by viruses.

26. Method according to claim 23 wherein the selection of said cells to be immortalized is performed by culture in HAT medium.

27. Method according to claim 24 wherein said fuseme cells and said mammalian cells to be immortalized are co-cultivated.

28. Hybridoma cell consisting of a fusion product of a fuseme cell and a mammalian cell to be immortalized.

29. Hybridoma cell according to claim 28 wherein the mammalian cell to be immortalized is a tumor cell.

30. Hybridoma cell according to claim 28 wherein the mammalian cell to be immortalized is a leukemic cell.

31. Hybridoma cell according to claim 28 wherein said fuseme cell is prepared from a B cell which has been conditionally immortalized by EBV.

32. Method for the generation of T cells directed against tumor cells comprising the following steps:

(a) providing fuseme cells and tumor cells to be immortalized;

(b) providing the tumor cells to be immortalized with immortalization genes from the fuseme cells;

(c) selecting for immortalized tumor cells;

(d) recovering the immortalized tumor cells, abolishing the conditional immortalization and co-culturing with peripheral mononucleated cells containing T cells of a patient from whom the tumor cell has been obtained or of a healthy donor; and (e) selecting for T cells which recognize the tumor cells employed in step (a).

33. Method according to claim 32 wherein lymphoma cells are used as said tumor cells.

34. Method for the preparation of hybridoma cells from a fuseme cell and a lymphocyte cell comprising the following steps:

(a) providing a fuseme cell and a lymphocyte cell;

(b) fusing the fuseme cell with the lymphocyte cell;

(c) selecting for conditionally immortalized hybridoma cells and optionally cloning individual hybridoma cells;

(d) expanding the hybridoma cells; and (e) abolishing the conditional immortalization.

35. Method according to claim 34 wherein the lymphocyte is contained in the peripheral mononucleated cells of a donor.

36. Method according to claim 34 wherein in said step (c) the selection is performed for conditionally immortalized hybridoma cells expressing an antibody having a particular specificity or containing a T cell receptor having a particular specificity.

* * * * *